United States Patent

Baldwin et al.

[11] Patent Number: 5,032,598

[45] Date of Patent: Jul. 16, 1991

[54] NITROGENS CONTAINING HETEROCYCLIC COMPOUNDS AS CLASS III ANTIARRHYTHMIC AGENTS

[75] Inventors: John J. Baldwin, Gwynedd Valley; David A. Claremon, Audubon; Jason M. Elliott, Blue Bell; Gerald S. Ponticello, Lansdale; David C. Remy, North Wales; Harold G. Selnick, Ambler, all of Pa.

[73] Assignee: Merck & Co., Inc., Rahway, N.J.

[21] Appl. No.: 447,949

[22] Filed: Dec. 8, 1989

[51] Int. Cl.$^5$ ............... A61K 31/445; C07D 401/06; C07D 409/04; C07D 409/14

[52] U.S. Cl. ............................. 514/318; 514/252; 514/253; 514/254; 514/255; 514/319; 514/821; 544/283; 544/284; 544/331; 544/361; 544/363; 544/364; 544/373; 544/376; 544/402; 544/405; 546/176; 546/194; 546/196; 546/198; 546/199; 546/200; 546/201; 546/209

[58] Field of Search ............ 546/194, 229, 232, 194, 546/229, 232; 514/318, 319, 821, 252, 253, 254, 255, 318, 319, 821; 544/361, 364, 376, 402, 403, 331, 283, 405

[56] References Cited

U.S. PATENT DOCUMENTS

| | | | |
|---|---|---|---|
| 4,544,654 | 10/1965 | Davey et al. | 514/210 |
| 4,629,739 | 12/1966 | Davey et al. | 514/605 |
| 4,721,809 | 1/1988 | Buzby et al. | 564/82 |
| 4,783,471 | 11/1988 | Carr et al. | 514/317 |
| 4,788,196 | 11/1988 | Cross et al. | 514/252 |
| 4,797,401 | 1/1989 | Kemp et al. | 514/255 |
| 4,804,662 | 2/1989 | Nickisch et al. | 514/252 |
| 4,806,536 | 2/1989 | Cross et al. | 514/252 |
| 4,806,555 | 2/1989 | Lamsford et al. | 514/652 |

FOREIGN PATENT DOCUMENTS

| | | |
|---|---|---|
| 235752 | 9/1987 | European Pat. Off. . |
| 242173 | 10/1987 | European Pat. Off. . |
| 281254 | 9/1988 | European Pat. Off. . |
| 284384 | 9/1988 | European Pat. Off. . |
| 285284 | 10/1988 | European Pat. Off. . |
| 288277 | 10/1988 | European Pat. Off. . |
| 296560 | 12/1988 | European Pat. Off. . |
| 300908 | 1/1989 | European Pat. Off. . |
| 307121 | 3/1989 | European Pat. Off. . |
| 3633977 | 4/1988 | Fed. Rep. of Germany . |

*Primary Examiner*—Cecilia Shen
*Attorney, Agent, or Firm*—Donald J. Perrella; William H. Nicholson; Joseph F. DiPrima

[57] ABSTRACT

Compounds of structural formula:

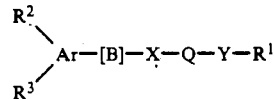

wherein Ar is an aromatic ring, B is a cyclic moiety fused to Ar of 5–7 members and Q is a nitrogen containing heterocycle, are antiarrhythmic agents.

9 Claims, No Drawings

NITROGENS CONTAINING HETEROCYCLIC COMPOUNDS AS CLASS III ANTIARRHYTHMIC AGENTS

SUMMARY OF THE INVENTION

This invention is concerned with novel compounds of the class with structural formula:

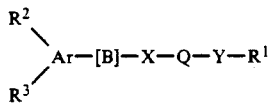

or a pharmaceutically acceptable salt thereof, wherein Ar is an aromatic ring, B is a 5-7 membered cyclic moiety fused to Ar, and X and Y are bridging groups such as alkylene, Q is a 5-7 membered nitrogen heterocycle such as piperidine or piperazine and $R^1$ is an aryl group. These compounds are useful in the treatment of arrhythmia.

The invention is also concerned with novel processes for preparing the novel compounds; pharmaceutical formulations comprising one or more of the novel compounds as an active antiarrhythmic agent either alone or in combination with other cardiovascular agents such as a $\beta$-blocker or other antiarrhythmic agent; and a method of treating arrhythmia by administration of one of the novel compounds or formulations thereof to a patient in need of such treatment.

BACKGROUND OF THE INVENTION

Arrhythmias often occur as complications to cardiac diseases such as myocardial infarction and heart failure. In a serious case, arrhythmias give rise to a ventricular fibrillation and can cause sudden death.

Though various antiarrythmic agents are now available on the market, those having both satisfactory effects and high safety have not been obtained. For example, antiarrythmic agents of Class I according to the classification of Vaughan-Williams which cause a selective inhibition of the maximum velocity of the upstroke of the action potential (Vmax) are inadequate for preventing ventricular fibrillation. In addition, they have problems regarding safety, namely, they cause a depression of the myocardial contractility and have a tendency to induce arrythmias due to an inhibition of the impulse conduction. Beta-adrenoceptor blockers and calcium antagonists which belong to Class II and IV respectively, have a defect that their effects are either limited to a certain type of arrhythmia or are contraindicated because of their cardiac depressant properties in certain patients with cardiovascular disease. Their safety, however, is higher than that of the antiarrhythmic agents of Class I.

Antiarrhythmic agents of Class III are drugs which cause a selective prolongation of the duration of the action potential without a significant depression of the Vmax. Drugs in this class are limited. Examples such as sotalol and amiodarone have been shown to possess Class III properties. Sotalol also possesses Class II effects which may cause cardiac depression and be contraindicated in certain susceptible patients. Also, amiodarone is severly limited by side effects. Drugs of this class are expected to be effective in preventing ventricular fibrillations. Pure class III agents, by definition, are not considered to cause myocardial depression or an induction of arrhythmias due to the inhibition of the action potential conduction as seen with Class I antiarrhythmic agents.

A number of antiarrhythmic agents have been reported in the literature, such as those disclosed in:
(1) EP No. 397,121-A,
(2) EP No. 300,908-A,
(3) EP No. 307,121,
(4) U.S. Pat. No. 4,629,739,
(5) U.S. Pat. No. 4,544,654,
(6) U.S. Pat. No. 4,788,196,
(7) EP application No. 88302597.5,
(8) EP application No. 88302598.3,
(9) EP application No. 88302270.9,
(10) EP application No. 88302600.7,
(11) EP application No. 88302599.1,
(12) EP application No. 88300962.3,
(13) EP application No. 235,752,
(14) DE No. 3633977-A1,
(15) U.S. Pat. No. 4,804,662,
(16) U.S. Pat. No. 4,797,401,
(17) U.S. Pat. No. 4,806,555,
(18) U.S. Pat. No. 4,806,536.

DETAILED DESCRIPTION OF THE INVENTION

The novel compounds of this invention have structural formula:

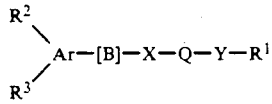

or a pharmaceutically acceptable salt thereof, wherein:
Ar is an aromatic ring selected from;
  (1) benzo,
  (2) thieno, and
  (3) furo, and
  (4) pyrrolo;
B is benzo or other carbocyclic or heterocyclic moiety of 5-7 members fused to the aromatic ring, Ar, with up to 3 variable members independently selected from:
  (1) $S-(O)_p$, wherein p is 0, 1, or 2,
  (2) $C(R)_2$ wherein the R groups are the same or different and represent hydrogen or $C_{1-6}$ alkyl,
  (3) C=O,
  (4) CHOR,
  (5) —O—, and
  (6) NR;
Q is a 5-7 membered heterocycle with one or two nitrogen atoms such as piperidine, piperazine, pyrrolidine, imidazolidine, hexahydroazepine, hexahydrodiazepine, or imidazole;
X is —CO—, —CONR(CR$_2$)m—, —SO$_2$— or —(CR$_2$)—$_m$ wherein m is 0, 1, 2 or 3;
Y is (CR$_2$)$_n$—; wherein n is 0, 1, 2 or 3
$R^1$ is hydrogen if Q is imidazolyl or if Q is other than imidazolyl, $R^1$ is pyridyl, benzimidazolyl, pyrimidinyl, phenyl, naphthyl, thienyl, thiazolyl, pyrazinyl, quinolinyl, quinoxalinyl, indolyl, or benzofuranyl, either unsubstituted or substituted with one or more of $R^2$, $R^3$ and/or $R^5$,
wherein:
$R^5$ is
  (1) —N(R)SO$_2$ C$_{1-6}$alkyl,
  (2) —N(R)SO$_2$(CH$_2$)mCO$_2$C$_{1-6}$alkyl, (3) —NO₂;
(4) —N(R)COC₁₋₆alkyl,
(5) —N(R)SO₂—C₆H₄—R
(6) —N(R)COC₆H₄R
(7) —C₂₋₆alkanoyl,
(8) CON(R)₂
(9) —CN,
(10) —CO₂C₁₋₆alkyl
(11) benzoyl, either unsubstituted or substituted with C₁₋₆alkyl, C₁₋₆alkoxy, halo such as Cl, Br, F, or I or hydroxy
(12) —NRCOO(C₁₋₆alkyl),
(13) —NRCOOphenyl either unsubstituted or substituted with C₁₋₆alkyl, C₁₋₆alkoxy, hydroxy or halo such as Cl, F, Br, or I,
(14) —NRCON(R)₂,
(15) —S(O)$_p$C₁₋₆alkyl, wherein p is 0, 1 or 2,
(16) —S(O)$_p$phenyl, either unsubstituted or substituted with C₁₋₆alkyl, C₁₋₆alkoxy, hydroxy, or halo such as F, Cl, Br, or I,
(17) phenyl, either unsubstituted or substituted with C₁₋₆alkyl, C₁₋₆alkoxy, halo such as Cl, Br, F, or I, or hydroxy,
(18) imidazolyl, or
(19) SO₂ N(R)₂;

R² and R³ are independently selected from:
(1) hydrogen,
(2) C₁₋₃alkyl either unsubstituted or substituted with
 (a)—N(R)₂
 (b)—CON(R)₂
 (c)—CO(C₁₋₆alkyl),
 (d)—O(C₁₋₆alkyl),
 (e)—OH, or
 (f)—S(O)p(C₁₋₆alkyl);
(3) C₁₋₃ alkoxy,
(4) —N(R)₂,
(5) halo such as Cl, Br, F, or I, or
(6) CF₃.

with the proviso that if R¹ is phenyl, with other than and an R⁵ substitutent, then one of R² or R³ in the

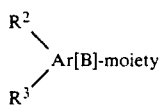

is R⁵.

One embodiment of the novel compounds of this invention comprises those wherein Q represents a 5–7 membered heterocycle and has a subgeneric structure

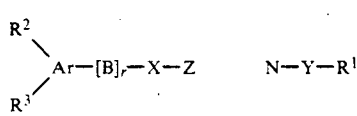

wherein Z is —CH< or —N< especially wherein Q represents piperazine or piperidine.

It is preferred that Ar be benzo or thieno and that B have the structure:

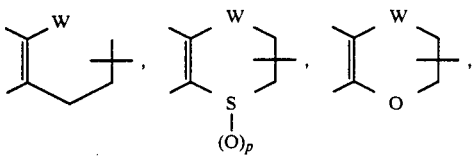

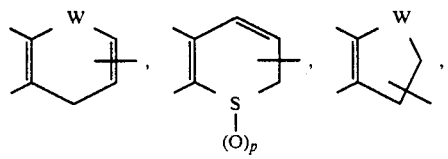

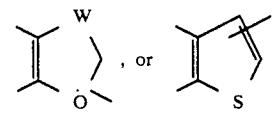

wherein W is C=O, CH₂ or CHOH. It is even more preferred that B have the structure:

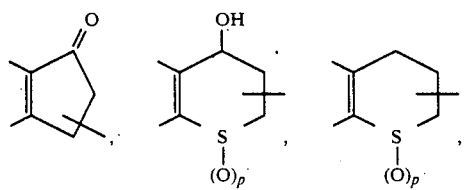

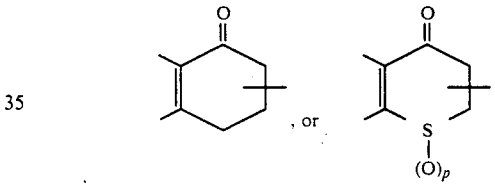

It is also preferred that R¹ be pyridyl, benzimidazolyl, pyrimidinyl or phenyl, either unsubstituted or substituted with R², R³ and/or R⁵, especially 2-pyridyl, 6-methyl-2-pyridyl, or 4-methanesulfonamidophenyl.

The term "alkyl", if the number of carbons is unspecified, means C₁₋₆alkyl and "alkyl" of three or more carbon atoms includes straight chain, branched chain and cycloalkyl.

Also included within the scope of the present invention are the non-toxic pharmaceutically acceptable salts of the novel compounds. Acid addition salts are formed by mixing a solution of the compound with a solution of a pharmaceutically acceptable non-toxic acid such as hydrochloric acid, fumaric acid, maleic acid, succinic acid, acetic acid, citric acid, tartaric acid, phosphoric acid, or the like.

Also included within the scope of this invention are diastereomers and enantiomers of the novel compounds and mixtures thereof.

The novel processes of this invention can be exemplified by the following reaction schemes.

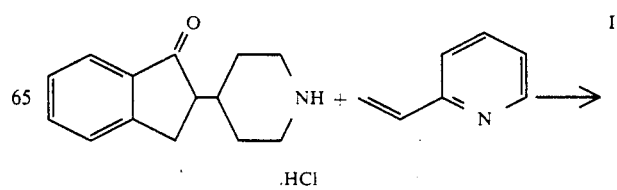

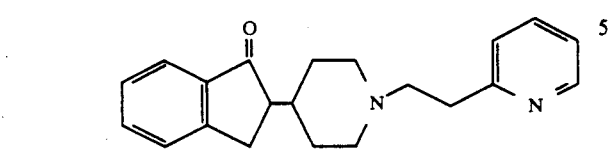

II

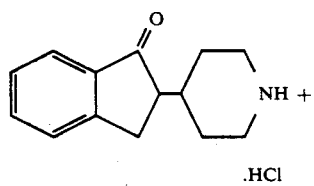
.HCl

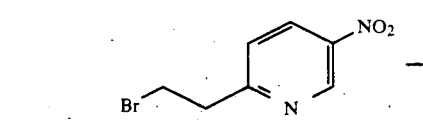

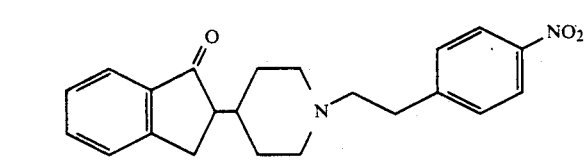

III

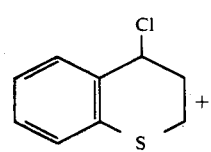

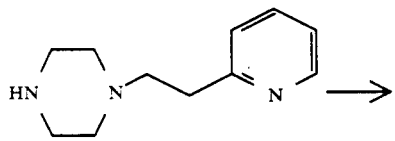

IV

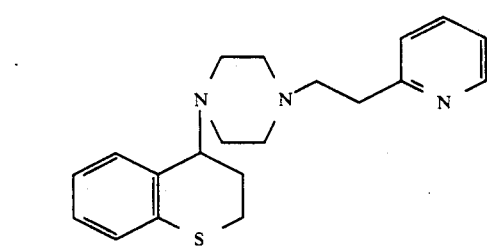

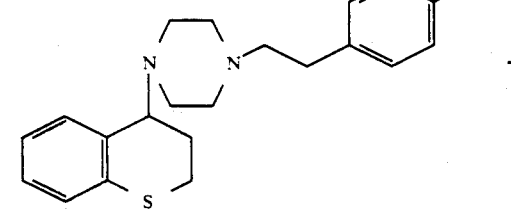

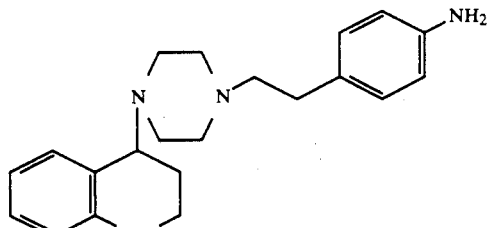

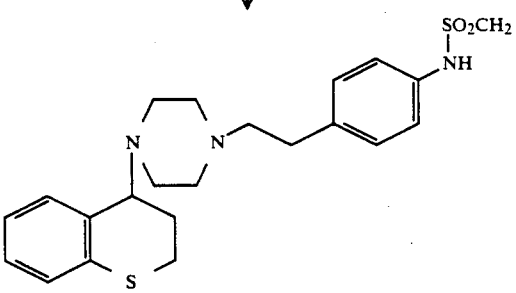

V

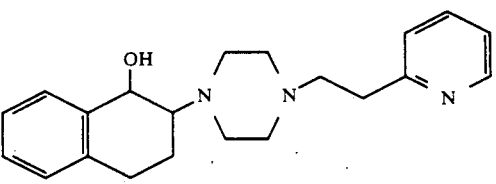

The process of Scheme I comprises addition of the piperidine across the vinyl group by heating a mixture of 1 part of the piperidine compound with about 1–2 parts of the vinyl compound in an aqueous lower alkanol such as methanol or ethanol in the presence of 1–2 parts of sodium or potassium acetate for about 10–20 hours at about reflux temperature.

Reaction Scheme II comprises N-alkylation of the piperidine molecule with a slight excess of the phenalkyl alkylating agent. Although the leaving group exemplified is bromo, equivalent leaving groups are chloro, mesyl, tosyl, or the like. The two reagents are heated at about reflux temperature in a suitable solvent, preferably one in which the reagents are soluble such as, in this case a lower alkanol, such as methanol, ethanol or propanol in the presence of an acid scavenger such as sodium or potassium bicarbonate or carbonate, an organic amine or an appropriate ion exchange resin for about 45 to 96 hours.

The process of Scheme III is similar to that of Scheme II except that a more suitable solvent is acetone, acetonitrile or methanol.

Scheme IV depicts alterations of substituents such as reduction of an aromatic nitro group to an amino which can be accomplished with standard reducing agents known in the art such as stannous chloride, or titanium trichloride, followed by sulfonylation with an alkanesulfonyl chloride by standard procedures.

Similarly reaction Scheme V is reduction of the tetralone carbonyl with a complex hydride such as lithium or sodium borohydride in methanol or lithium aluminum hydride in THF.

The compounds of the present invention have the pharmacological properties required for the antiarrhythmic agents of Class III, namely the prolongation of the myocardial action potential in vitro without a significant depression of the Vmax and with the prolongation of QTc-interval in anesthetized dogs. Moreover, the effects of many of the novel compounds are much more potent than the reference drug, sotalol.

The compounds of the present invention are effective in treating and preventing all types of arrhythmias including ventricular and atrial (supraventricular) arrhythmias. The compounds of the present invention are especially useful to control reentrant arrhythmias and prevent sudden death due to the ventricular fibrillation.

In the novel method of this invention of treating arrhythmia, a novel compound or pharmaceutically acceptable salt thereof, is administered in an amount ranging from about 0.0001 to about 20 mg per kg of body weight per day, preferably from about 0.001 to about 10 mg per kg of body weight per day in a single dose or in 2 to 4 divided doses.

The novel compounds of this invention can be administered as the sole active ingredient or in combination with other antiarrhythmic agents or other cardiovascular agents.

The compounds, or pharmaceutically acceptable salts thereof, of the present invention, in the described dosages, are administered orally, intraperitoneally, subcutaneously, intramuscularly, transdermally, sublingually or intravenously. They are preferably administered orally, for example in the form of tablets, troches, capsules, elixirs, suspensions, syrups, wafers, chewing gum, or the like prepared by art recognized procedures. The amount of active compound in such therapeutically useful compositions or preparations is such that a suitable dosage will be obtained.

EXAMPLE 1

2-[1-(2-Pyridylethyl)-4-piperidyl]-1-indanone dihydrochloride

Step A: Preparation of 2-(4-piperidyl)-1-indanone hydrochloride

To a solution of 2.73 g (0.0119 mol) of 2-(1-methyl-4-piperidyl)-1-indanone in 100 ml of 1,2-dichloroethane cooled in an ice bath was added 1.72 g (0.012 mol) of α-chloroethyl chloroformate dropwise. The solution was allowed to warm to room temperature and then was refluxed for 2 hours. TLC indicated the reaction was not complete. An additional 0.86 g (0.006 mol) of α-chloroethyl chloroformate was added to the cooled mixture, after which it was refluxed for 2 hours. The 1,2-dichloroethane was removed under reduced pressure, and the residue was chromatographed on silica gel using ethyl acetate as an eluant. Evaporation of the eluant gave 1.90 gm of a clear oil. The oil was dissolved in 50 mL of methanol and was refluxed for 10 hours. Evaporation of the methanol afforded 1.60 g of 2-(4-piperidyl)-1-indanone hydrochloride.

Step B: Preparation of 2-[1-(2-pyridylethyl)-4-piperidyl]-1-indanone dihydrochloride A mixture of 0.251 g (0.001 mol) of 2-(4-piperidyl)-1-indanone hydrochloride, 0.21 g (0.002 mol) of 2-vinylpyridine, 0.272 g (0.002 mol) sodium acetate trihydrate, 2 mL of water, and 2 mL of methanol was stirred and refluxed for 20 hours. The solvent was evaporated in vacuo and the residue was dissolved in ethyl acetate and dried over magnesium sulfate. The product was isolated in pure form by chromatography on silica gel using 5% methanol in chloroform. A hydrochloride salt was prepared and was recrystallized from ethanol to give 2-[1-(2-pyridylethyl)-4-piperidyl]-1-indanone dihydrochloride, mp 195°–196° C.

Anal. Calcd. for $C_{21}H_{24}N_2O.2HCl.0.4H_2O$: C, 62.97; H, 6.74; N, 6.99. Found C, 63.05; H, 6.61; N, 6.90.

EXAMPLE 2

2-[1-(4-Nitrophenethyl)-4-piperidyl]-1-indanone dihydrochloride

A mixture of 0.46 g (0.00183 mol) of 2-(4-piperidyl)-1-indanone hydrochloride, 0.578 g (0.00251 mol) of p-nitrophenethyl bromide, 0.422 g (0.00502 mol) sodium bicarbonate and 20 mL of ethanol was stirred and refluxed for 72 hours. The ethanol was removed by evaporation, and the residue was partitioned between ethyl acetate and water. The ethyl acetate phase was washed with water, dried over magnesium sulfate, filtered, and the ethyl acetate removed. The residue was purified by chromatography on silica gel using 2.5% methanol in chloroform as an eluant. Evaporation of the solvent gave a crystalline product that was converted to a hydrochloride salt. Recrystallization from ethanol gave 2-[1-(4-nitrophenethyl)-4-piperidyl]-1-indanone hydrochloride, mp 259°–261° C.

Anal. Calcd. for $C_{22}H_{24}N_2O_3.HCl.0.25H_2O$: C, 65.18; H, 6.34; N, 6.91. Found C, 65.21; H, 6.06; N, 6.78.

EXAMPLE 3

2-[1-(4-Methanesulfonamidophenethyl)-4-piperidyl]-1-indanone hydrochloride

A mixture of 0.54 g (0.0022 mol) of 2-(4-piperidyl)-1-indanone hydrochloride, 0.73 g (0.0025 mol) of 2-[4-(methanesulfonamidophenyl]-1-ethanol methanesulfonate, 0.45 g (0.0054 mol) of sodium bicarbonate and 20 mL of ethanol was stirred and refluxed for 14 hours. The ethanol was removed and the residue was dissolved in ethyl acetate. This solution was washed with water, dried over MgSO$_4$, filtered, and the solvent removed. A hydrochloride salt was prepared and was recrystallized from ethanol to give 2-[1-(4-methanesulfonamidophenethyl)-4-piperidyl]-1-indanone hydrochloride, m.p. 258°–261° C.

Anal. Calcd. for $C_{23}H_{28}N_2O_3S.HCl.0.25H_2O$: C, 60.91; H, 6.56; N, 6.18. Found C, 60.83; H, 6.42; N, 6.16.

EXAMPLE 4

4-{[4-(2-Pyridylethyl)]-1-piperazinyl}thiochromane trihydrochloride

Thionyl chloride (4 mL) was added to 0.50 g (0.003 mol) of thiochroman-4-ol. After the reaction had subsided, the excess thionyl chloride was removed on a rotary evaporator. The residue was dissolved in 20 mL of acetone, and 0.67 g (0.0035 mol) of 4-(2-pyridyethyl)-piperazine and 0.57 g (0.00415 mol) of powdered potassium carbonate were added. The stirred mixture was refluxed for 46 hours. The acetone was removed by evaporation and the residue was partitioned between ethyl acetate and water. The organic phase was washed with water, dried over MgSO$_4$, filtered, and the solvent removed to afford 1.01 g of clear oil. Flash chromatography on silica gel using 3% methanol in chloroform gave 4-{[4-(2-pyridylethyl)]-1-piperazinyl}thiochromane. A hydrochloride salt was prepared and recrystallized from ethanol: m.p. 183°-185° C.

Anal. Calcd. for $C_{20}H_{25}N_3S.3HCl.H_2O$: C, 51.45; H, 6.48; N, 9.00. Found C, 51.47; H, 6.52; N, 8.95.

EXAMPLE 5

4-{[4-(p-Nitrophenethyl)-1-piperazinyl]}thiochromane hydrochloride

Thionyl chloride (5 mL) was added to 1.0 g (0.006 mol) of thiochroman-4-ol. After the reaction had subsided the excess thionyl chloride was removed on a rotary evaporator. To the residue was added 1.64 g (0.007 mol) of 4-(p-nitrophenethyl)piperazine, 1.14 g (0.0083 mol) of powdered potassium carbonate, and 30 mL of acetone. The mixture was stirred and refluxed for 40 hours. The acetone was removed by evaporation in vacuo and the residue was partitioned between ethyl acetate and water. The organic phase was washed with water, dried over $MgSO_4$, filtered, and the solvent removed. Flash chromatography of the residue on silica gel using 3% methanol in chloroform gave 0.47 g of crystalline material. A hydrochloride salt, prepared in ethanol, was recrystallized from water to give the intermediate 4-{[4-(p-nitrophenethyl)-1-piperazinyl]}-thiochromane hydrochloride, m.p. 214°-215° C.

Anal. Calcd. for $C_{21}H_{25}N_3O_2S.HCl.0.5H_2O$: C, 58.82; H, 6.34; N, 9.80. Found C, 58.92; H, 6.26; N, 9.80.

EXAMPLE 6

N-{4-(4-Thiochromanyl)-1-piperazinyl]ethylphenyl} methanesulfonamide

To a solution of 1.0 g (0.00261 mol) of 4-{[4-(p-nitrophenethyl)-1-piperazinyl]}thiochromane in 25 mL of ethyl acetate was added 2.5 g of stannous chloride dihydrate. The mixture was stirred 30 minutes at room temperature and then was refluxed for 30 minutes. An additional 2.5 gm of stannous chloride dihydrate was added and the mixture was refluxed an additional hour. To the cooled solution was added 50 ml of 20% aqueous sodium hydroxide solution. The mixture was stirred vigorously, and the ethyl acetate was decanted. The mixture was re-extracted with ethyl acetate and the combined extracts were washed with water, dried ($MgSO_4$), and filtered. Evaporation of the solvent gave 0.68 gm (74%) of a clear oil. This oil was dissolved in 3 mL of methylene chloride and was treated with 0.25 g (0.00212 mol) of methanesulfonyl chloride. After stirring at room temperature for 4 hours, the solvent was evaporated and the residue was converted to a hydrochloride salt. Recrystallization from methanol gave the title compound; m.p. 213°-215° C.

Anal. Calcd. for $C_{22}H_{29}N_3O_2S_2.2HCl$: C, 52.37; H, 6.19; N, 8.33. Found C, 52.39; H, 6.25; N, 8.28.

EXAMPLE 7

2-[4-(4-Nitrophenethyl)-piperazin-1-yl]-1-tetralone

Method A

To a solution of 4.7 g (0.002 mole) 1-(p-nitrophenethyl)piperazine and 0.25 g (0.0025 mole) triethylamine in 10 ml acetone was added 0.45 g (0.002 mole) 2-bromo-α-tetralone. The solution was stirred under $N_2$ at room temperature for 16 hours. The mixture was filtered. The solid was treated with saturated $NaHCO_3$ solution and extracted with $CH_2Cl_2$. The $CH_2Cl_2$ solution was dried over $Na_2SO_4$, filtered and concentrated. The solid residue was dissolved in $CH_2Cl_2/CH_3OH$ and acidified with ethanolic HCl. The solvent was removed in vacuo the resulting solid residue was treated with boiling ethanol. The dihydrochloride was filtered off and dried to give 0.095 g (10.5% yield) m.p. 222°-223° C.

Anal. Calcd. for $C_{22}H_{25}N_3O_3.2HCl.\frac{3}{4}H_2O$: C, 56.71; H, 6.17; N, 9.02. Found C, 56.64; H, 6.12; N, 9.06.

Method B

A solution of 2.25 g (0.01 mole) 2-bromo-α-tetralone and 2.35 g (0.01 mole) 1-(p-nitrophenethyl)-piperazine in 15 ml acetone was stirred and heated at reflux for 6 hours. The mixture was filtered and treated as in Method A. 1.06 g (28% Yield) free base was obtained.

Employing the procedure substantially as described in Example 7, but substituting for the 2-bromo-α-tetralone and the 1-(p-nitrophenethyl)-piperazine used therein the tetralones and piperazines described in Table I there were produced the piperazinyl tetralones also described in Table I in accordance with the following reaction scheme:

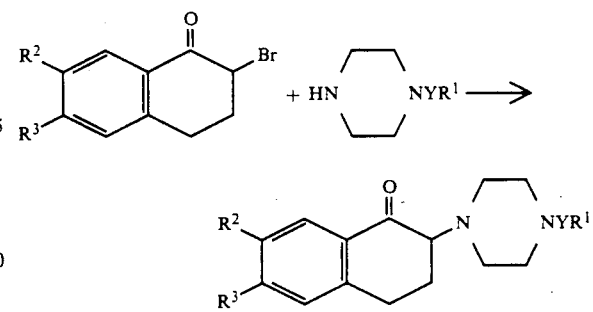

TABLE I

| Example | R² | R³ | —Y—R¹ | salt | m.p.(°C.) |
| --- | --- | --- | --- | --- | --- |
| 8 | H | H | (2-pyridylethyl) | 3HCl.0.75H₂O | 196–199 |
| 9 | NO₂⁽¹⁾ | H | (4-nitrophenethyl) | 2HCl.0.5H₂O | 245–248 |

TABLE I-continued

| Example | R² | R³ | —Y—R¹ | salt | m.p.(°C.) |
|---|---|---|---|---|---|
| 10 | H | H | propyl-phenyl-NHSO₂CH₃ | 2HCl.0.5H₂O | 166–169.5 |
| 11 | NO₂[1] | H | propyl-phenyl | HBr.0.5H₂O | 234–236 |
| 12 | NO₂[1] | H | propyl-(2-pyridyl) | 3HCl | 171–181 |
| 13 | CH₃SO₂NH—[1] | H | propyl-phenyl | 2HCl.0.5H₂O | 216–219.5 |
| 14 | CH₃SO₂NH—[1] | H | propyl-(2-pyridyl) | 2HCl | 226–229 |
| 15 | H | CH₃SO₂NH—[1] | propyl-phenyl-NO₂ | HBr | 286(dec.) |

[1]The 2-bromo-6- and 7-nitro and methanesulfonamido compounds required as starting materials are prepared as described below for 2-bromo-7-nitro-1-tetralone and 2-bromo-7-methanesulfonamido-α-tetralone.

7-Amino-1-tetralone:

A solution of 2 g (0.0105 mole) 7-nitro-1-tetralone in 120 ml ethanol was hydrogenated under <5 psi H₂ pressure using Raney Ni as catalyst. The solution was filtered with the aid of super gel and concentrated under reduced pressure to give the 7-amino-1-tetralone.

7-Methanesulfonamide-1-tetralone:

To a solution of 7-amino-1-tetralone in 30 ml CH₂Cl₂ was added 1.03 g (0.013 mole) pyridine and 1.33 g (0.0116 mole) methanesulfonyl chloride. The solution was stirred at room temperature for 3 hours, saturated NaHCO₃ solution was added. The CH₂Cl₂ solution was separated and washed with H₂O. The resulting solution was dried over Na₂SO₄ (anhydrous), filtered, concentrated in vacuo and recrystallized from abs. ethanol to give 1.45 g (58% yield) of 7-methanesulfonamido-1-tetralone.

2-Bromo-7-nitro-1-tetralone:

To a suspension of 9.56 g (0.05 mol) of 7-nitro-1-tetralone in 250 mL of ether was added bromine dropwise. The progress of the reaction was followed by thin layer chromatography (fl. silica gel/CH₂Cl₂). When all of the starting material had been consumed, the mixture was concentrated and cyclohexane was added. The white solid was removed by filtration to afford 2.25 g of 2-bromo-7-nitrotetralone, mp 94°–96° C.

2-Bromo-7-methanesulfonamido-1-tetralone:

To a solution of 1.4 g (0.00585 mol) of 7-methanesulfonamidotetralone in 20 mL of methylene chloride was added dropwise a solution of 0.94 g (0.0059 mol) of bromine in 5 mL of methylene chloride. The process of the reaction was followed by thin layer chromatography (fl. silica gel/CH₂Cl₂). A few additional drops of the bromine solution were added to completely consume the starting material. The solution was evaporated to dryness to give 2.0 g of 2-bromo-7-methanesulfonamido-1-tetralone, mp 87°–92° C.

EXAMPLE 16

1-Hydroxy-2-[4-(4-nitrophenethyl)piperazin-1-yl]tetralin

To a solution of 0.13 g (0.00034 mole) 2-[4-(4-nitrophenethyl)-piperazin-1-yl]-1-tetralone in 30 ml CH₃OH was added 0.081 g (0.00214 mole) sodium borohydride in small portions. The solution was stirred at room temperature for 17 hours. The solvent was removed under reduced pressure. Water was added to the residue. Crude solid product was filtered off and recrystallized from ethyl acetate/n-hexane to give 30 mg product. NMR and TLC of this material indicated it to be a mixture of 2 isomers. HPLC showed the isomer ratio to be 50–48. This mixture was converted to its dihydrochloride. m.p. 155°–159° C.

Anal. Calcd. for $C_{22}H_{26}N_3O_3.2HCl$: C, 57.14; H, 6.32; N, 9.09. Found C, 57.39; H, 6.47; N, 8.94.

EXAMPLE 17

1-Hydroxy-2-[4-(2-pyridyl-2-ethyl)piperazin-1-yl]tetralin.3HCl.0.75 H₂O, m.p. 220°–223° C. (isomer ratio 52:45) was prepared employing the procedure substantially as described in Example 16.

EXAMPLE 18

5,6-Dihydro-5-[4'-(2-(2-pyridyl)ethyl)piperazin-1'-yl]methylthieno[2,3-b]thiopyran-4-one trihydrochloride-hemihydrate Step A: Preparation of 5,6-dihydro-5-dimethylaminomethylthieno[2,3-b]thiopyran-4-one hydrochloride A mixture of 5,6-dihydrothieno[2,3-b]thiopyran-4-one (12.5 g, 0.074 mol), paraformaldehyde (7.5 g, 0.25 mol), dimethylamine-hydrochloride (40 g, 0.49 mol) and acetic acid (2 ml) was heated with stirring at 100° C. for 1 hour. After allowing to cool to room temperature, the solid was triturated with ethanol and the solid was collected on a filter to yield 16.3 g (83%) of the title compound. An analytical sample was prepared by crystallization from 95% ethanol and filtration through a pad of norite-ducco-supercel to yield product with mp 155°–157° C. Anal. Calc'd. for $C_{10}H_{13}NOS_2 \cdot HCl$.

|   | Calc'd | Observed |
|---|---|---|
| C | 5.31 | 5.42 |
| H | 41.53 | 45.12 |
| N | 5.35 | 5.37 |

Step C: Preparation of 5,6-dihydro-5-[4'-(2-(2-pyridyl)ethyl)piperazin-1'-yl]methylthieno[2,3-b]thiopyran-4-one trihydrochloride hemihydrate Under $N_2$, a mixture of product from Step B (0.26 g, 0.0014 mol); 1-(2-(2-pyridyl)ethyl)piperazine (0.35 g, 0.0018 mol) and $Al_2O_3$ (0.35 g) in benzene (10 ml) was stirred at room temperature. After 18 hours, the mixture was filtered, and the solution concentrated to dryness. The residue was chromatographed on silica gel (Still column, 50 mm) and the product was eluted with 5% methanol/chloroform to 60 mg (9%) of free base. The compound was crystallized as the HCl salt from ethanol to yield 4; mp 165° C. Anal. Calc'd. for $C_{19}H_{23}N_3OS_2 \cdot 3HCl \cdot \frac{1}{2} H_2O$

|   | Calc'd | Observed |
|---|---|---|
| N | 8.39 | 8.54 |
| C | 46.25 | 46.38 |
| H | 5.60 | 5.53 |

EXAMPLE 19

5,6-Dihydro-5-[N-2-methylimidazoyl]methylthieno[2,3-b]thiopyran-4-one

Under $N_2$, a mixture of 5,6-dihydro-5-methylenethieno[2,3-b]thiopyran (0.55 g, 0.003 mol), 2-methylimidazole 0.25 g, 0.006 mol), $Al_2O_3$ act. III (0.7 g) in benzene (15 ml) was stirred at room temperature. After 4 hours, the reaction was filtered and the solid was washed with ethylacetate. The organic filtrate was washed with $H_2O$, dried, filtered and concentrated to dryness. The residue was chromatographed on silica gel (Still column, 50 mm). The product was eluted with 2.5% $CH_3OH—CHCl_3$ with 0.25% aq. $NH_3$. The compound was crystallized from $CH_2Cl_2$-n-butyl chloride to yield 0.19 g (24%) of product. mp 135°–136° C. Anal. Cacl'd. for $C_{12}H_{16}N_2OS_2$.

|   | Calc'd | Observed |
|---|---|---|
| N | 10.6 | 10.49 |
| C | 54.52 | 54.12 |
| H | 4.58 | 4.49 |

EXAMPLE 20

2-(N-2-methylimidazoyl)methyl-6-methoxytetral-1-one

Step A: Preparation of 2-dimethylaminomethyl-6-methoxytetral-1-one

Under $N_2$, a mixture of 6-methoxytetral-1-one (0.45 g, 0.0028 mol), paraformaldehyde (0.28 g, 0.0095 mol), dimethylamine-hydrochloride (1.5 g, 0.018 mol) and acetic acid (0.8 ml) was heated at 100° C. After 1.5 hours, the reaction was cooled to room temperature, the solid was triturated with ethanol, filtered and the solids collected to yield 0.5 g (77%) of product.

Step B: Preparation of 2-methylene-6-methoxytetral-1-one

Under $N_2$, a mixture of product from Step A (0.21 g, 0.0009 mol) in DMF (25 ml) was heated at 100° C. After 1 hour, the reaction was cooled to room temperature, poured in $H_2O$, and extracted with ethyl acetate (3×). The organic layer was washed with $H_2O$, saturated NaCl, dried, filtered and concentrated to dryness to yield 170 mg (100%) of product.

Step C: Preparation of 2-(N-2-methylimidazoyl)-methyl-6-methoxytetral-1-one

A mixture of product from Step B (170 g, 0.001 mol), 2-methylimidazole (0.08 g, 0.001 mol), $Al_2O_3$ act. III (0.25 g) in benzene (5 ml) was stirred at room temperature. After 2 hours, 2-methylimidazole (0.08 g) was added and the reaction stirred at room temperature. After 18 hours, the reaction was filtered through super cel and the filter pad washed with ethylacetate. The organic layer was washed with $H_2O$, dried, filtered and concentrated to dryness. The residue was chromatographed on silica gel (Still column, 20 mm) and the product eluted with 5% $CH_3OH— CHCl_3$. The solid was crystallized from $CH_2Cl_2$—n— butyl chloride to yield 0.13 g (48%) of product; mp 163°–165° C. Anal. Calc'd. for $C_{16}H_{18}N_2O_2$.

|   | Calc'd | Observed |
|---|---|---|
| N | 10.36 | 10.16 |
| C | 71.09 | 70.79 |
| H | 6.71 | 6.49 |

EXAMPLE 21

5,6-Dihydro-4H-4-hydroxy-5-[(2-methyl-1H-imidazol-1-yl)-methyl]thieno[2,3-b]thiopyran(α-Isomer, and β-Isomer Sodium borohydride, 0.22 g (0.0057 m) was added to a stirred solution of 5,6-dihydro-5-[(2-methyl-1H-imidazol-1-yl)methyl]thieno[2,3-b]thiopyran-4-one, 1.14 g (0.0043 m), in absolute ethanol (45 ml). After refluxing for 2.5 hours, the mixture was treated with 5% sodium hydroxide solution (10 ml) and concentrated in vacuo to remove ethanol. The residue was distributed between ethyl acetate (50 ml) and water (25 ml), the aqueous layer was separated and extracted with ethyl acetate (2×35 ml). The combined extracts were washed twice with water, dried over sodium sulfate and concentrated in vacuo to yield 0.83 g (72%) of amorphous tan solid of a mixture of α and β-isomers. The mixture was chromatographed on a 50 mm diameter flash column using silica gel 60 (E. Merck 230–400 mesh) and eluting with 1% methanol/CHCl$_3$ saturated with ammonia. The α-isomer weighed 0.18 g and melted at 240°–241.5° C. after recrystallization from ethanol. Anal. Calc'd. for C$_{12}$H$_{14}$N$_2$OS$_2$: C, 54.11; H, 5.30; N, 10.52 Found: C, 53.89; H, 5.11; N, 10.37. The β-isomer weighed 0.30 g and melted at 155.5°–157.5° C. after recrystallization from ethanol-water. Anal. Calc'd. for C$_{12}$H$_{14}$N$_2$OS$_2$: C, 54.11; H, 5.30; N, 10.52. Found: C, 53.87; H, 5.18; N, 10.38. Based on PMR studies, the α-isomer is cis, and the β-isomer is trans.

EXAMPLE 22

6-Methanesulfonamido-2-(1-[2-pyridylethyl]-4-piperidyl)indan-1-one dihydrochloride Step A: Preparation of 6-Nitro-2-(1-methyl-4-piperidyl)-1-oxo-2-indanecarboxamide To an ice cold solution of 2-(1-methyl-4-piperidyl)-1-oxo-2-indanecarboxamide hydrochloride (5.5 g, 0.0178 mol) in 27 mL of concentrated sulfuric acid was added dropwise over 5 minutes 2.20 g of 90% nitric acid dissolved in 6.8 mL of cold concentrated sulfuric acid. After the addition was complete, the solution was stirred at 0° C. for two hours and then was poured onto ice. The solution was made basic by the addition of solid sodium bicarbonate, and the mixture was extracted with three 100 mL portions of chloroform. The combined chloroform extracts were washed with water, dried over magnesium sulfate, filtered, and the solvent was removed under reduced pressure. The residue was recrystallized from absolute ethanol to give 4.42 g (78% yield)) of 6-nitro-2-(1-methyl-4-piperidyl)-1-oxo-2-indane carboxamide, mp 189°–190° C.

Anal. Cal'd. for C$_{16}$H$_{19}$N$_3$O$_4$: C, 60.55; H, 6.04; N, 13.24. Found: C, 60.72; H, 6.05; N, 13.18.

Step B: Preparation of 6-Nitro-2-(1-methyl-4-piperidyl)-indan-1-one

A solution of 4.42 g of 6-nitro-2-(1-methyl-4-piperidyl)-1-oxo-2-indanecarboxamide in 60 mL of 6N hydrochloric acid was stirred and refluxed for one hour. The solution was cooled in an ice bath and made basic by the addition of 20% aqueous sodium hydroxide. The mixture was extracted with three 100 mL portions of ether. The combined extracts were dried over magnesium sulfate, filtered, and the ether was removed under reduced pressure to give 3.72 g (97%) of 6-nitro-2-(1-methyl-4-piperdyl)-indan-1-one as a low melting crystalline solid.

Step C: Preparation of 6-Nitro-2-(4-piperidyl)indan-1-one hydrochloride

To a stirred, ice-cooled solution of 0.71 g (0.00259 mol) of 6-nitro-2-(1-methyl-4-piperidyl)indan-1-one in 20 mL of 1,2-dichloroethane was added 0.67 g (0.0052 mol) of diisopropylethylamine and 0.74 g (0.0052 mol) of 1-chloroethyl chloroformate. After the addition was complete, the solution was refluxed for one hour. The cooled solution was washed with two portions of 2N HCl, water, and then was dried over magnesium sulfate. After filtration, the solvent was removed under reduced pressure. The residual oil was purified by filtration through a silica gel column using ethyl acetate to elute the column. Evaporation of the eluant gave 0.95 g (100%) of the intermediate urethane. A solution of 2.0 g of this urethane in 100 mL of absolute methanol was stirred and refluxed for one hour. Evaporation of the methanol gave 6-nitro-2-(4-piperidyl)-indan-1-one hydrochloride. The solid was triturated with isopropyl alcohol and was collected by filtration to give 1.25 g (81%) of product.

Step D: Preparation of 6-Nitro-2-(1-[2-pyridylethyl]-4-piperidyl)indan-1-one

A mixture of 0.60 g (0.0020 mol) of product from Step C, 0.22 g (0.0040 mol) of 2-vinylpyridine and 0.28 g (0.0040 mol) of sodium acetate trihydrate in 8 mL of aqueous methanol (1:1 v:v) was stirred and refluxed for 7 hours. An additional 0.106 g of 2-vinylpyridine and 0.14 g of sodium acetate trihydrate was added, and the mixture was stirred and refluxed for 9 hours. The mixture was evaporated to dryness, and the residue was extracted with chloroform. Evaporation of the chloroform extracts gave 0.70 g of oil that was purified by flash chromatography on silica gel using 5% CH$_3$OH in chloroform to elute the column. Evaporation of the eluate gave 0.40 g of 6-nitro-2-(1-[2-pyridyethyl]-4-piperidyl)indan-1-one.

Step E: Preparation of 6-Methanesulfonamido-2-(1-[2-pyridylethyl]-4-piperidyl)indan-1-one A solution of 0.40 g of product from Step D in 20 mL of ethanol and 20 mL of tetrahydrofuran was hydrogenated at 10 psi over Raney nickel catalyst. After 2 hours, the catalyst was removed by filtration, and the solvent was removed under reduced pressure to give 0.35 g of crystalline 6-amino-2-(1-[2-pyridylethyl]-4-piperidyl)indan-1-one.

Step F:

To a solution of 0.35 g (0.00104 mol) of product from Step E in 5 mL of pyridine was added 0.131 g (0.00115 mol) of methanesulfonyl chloride. After stirring at room temperature for one hour, the pyridine was removed under reduced pressure. After adding 10 mL of an aqueous saturated sodium bicarbonate solution to the residue, it was extracted with three portions of ethyl acetate. These extracts were combined and dried over MgSO$_4$. Removal of the solvent afforded 0.374 g (87%) of the free base of the product. A hydrochloride salt was prepared and recrystallized from methanol to give 6-methanesulfonamido-2-(1-[2-pyridylethyl]-4-piperidyl)indan-1-one dihydrochloride.0.5H$_2$O: mp 224°–226° C.

Anal. Cal'd. for C$_{22}$H$_{27}$H$_3$O$_3$S.2HCl.0.5H$_2$O: C, 53.33; H, 6.10; N, 8.48. Found: C, 53.11; H, 5.76; N, 8.40.

EXAMPLE 23

6-Methanesulfonamido-2-(1-[4-methanesulfonamidophenethyl]-4-piperidyl)indan-1-one hydrochloride Step A: Preparation of 6-Methanesulfonamido-2-(1-methyl-4-piperidyl)indane-1-one A solution of 1.86 g (0.0068 mol) of 6-nitro-2-(1-methyl-4-piperidyl)indan-1-one in 50 mL of absolute ethanol and 50 mL of tetrahydrofuran was hydrogenated at 10 psi over Raney nickel catalyst. After 2.5 hours, the catalyst was removed by filtration and the solvent was evaporated to give 1.76 g of crystalline 6-amino-2-(1-methyl-4-piperidyl)indan-1-one. To a solution of 1.04 g (0.00426 mol) of the 6-amino compound in 20 mL of methylene chloride and 3.4 g of pyridine was added 0.61 g (0.005 mol) of methanesulfonyl chloride. The mixture was stirred at room temperature for two hours, after which time it was poured onto water and made basic by the addition of a saturated sodium bicarbonate solution. The mixture was concentrated to dryness in vacuo, and the solid residue was extracted with two 50 mL portions of methylene chloride. Evaporation of the methylene chloride gave 1.56 g of 6-methanesulfonamido-2-(1-methyl-4-piperidyl)indane-2-one as a colorless foam.

Step B: Preparation of 6-Methanesulfonamido-2-(4-piperidyl)indan-1-one hydrochloride To a solution of 1.35 g (0.00419 mol) of 6-methanesulfonamido-2-(1-methyl-4-piperidyl)indan-1-one in 46 mL of 1,2-dichloroethane was added 1.35 g (0.0063 mol) of 1,8-bis(dimethylamino)naphthalene. The solution was cooled in an ice bath and 1.80 g (0.0126 mol) of 1-chloroethylchloroformate was added dropwise over 5 minutes. The mixture was allowed to warm to room temperature and then was refluxed for 5 hours. The cooled mixture was filtered through a small column of silica gel using methylene chloride to wash the column. The eluate was evaporated in vacuo. The residual 1.35 g of thick oil was dissolved in 10 mL of methanol, and the solution was refluxed for 24 hours. Evaporation of the methanol and crystallization of the residue from methanol afforded 6-methanesulfonamido-2-(4-piperidyl)indan-1-one hydrochloride as a hemi methanol solvate salt: mp 254°–256° (dec.).

Anal. Cal'd. for $C_{15}H_{20}N_2O_3S \cdot HCl \cdot 0.5CH_3OH$: C, 51.58; H, 6.42; N, 7.76. Found: C, 51.69; H, 6.36; N, 8.00.

Step C: Preparation of 6-Methanesulfonamido-2-(1-[4-methanesulfonamidophenethyl]-4-piperidyl)indan-1-one hydrochloride methanol solvate A mixture of 0.100 g (0.00029 mol) of 6-methanesulfonamido-2-(4-piperidyl)indan-1-one hydrochloride, 0.073 g (0.00087 mol) of sodium bicarbonate, 0.128 g (0.00044 mol) of 4-methanesulfonamidophenethyl alcohol mesylate, 15 mg of potassium iodide, and 10 mL of acetonitrile was stirred and refluxed for 32 hours. The cooled solution, transferred to a separatory funnel using 25 mL of ethyl acetate, was washed with water and then with brine. The organic phase was extracted with three 4 mL portions of 1N HCl. The combined acid extracts were made basic by addition of solid sodium bicarbonate, and the basic phase was extracted with three 30 mL portions of ethyl acetate. The combined organic extracts were dried over magnesium sulfate, filtered, and the solvent was removed under reduced pressure to afford 0.125 g (86%) of product. A hydrochloride salt was prepared in methanol; mp 130°–135° (foams).

Anal. Cal'd. for $C_{24}H_{31}N_3O_5S_2 \cdot HCl \cdot CH_3OH$: C, 52.29; H, 6.32; N, 7.32. Found: C, 52.64; H, 6.43; N, 7.03.

EXAMPLE 24

1-(Indole-5-carbonyl)-4-phenethylpiperazine

Indole-5-carboxylic acid (57 mg, 0.35 mmol) was dissolved in THF(2 ml) and DMF (1 drop), then oxalyl chloride (37 μl, 54 mg, 0.42 mmol) was added. The mixture was stirred at room temperature for 3 hours, the solvent was evaporated under reduced pressure and the residue was dissolved in DMF (2 ml) and added to a stirred solution of 1-phenethylpiperazine (66 mg, 0.35 mmol) and diisopropylethylamine (91 μl, 68 mg, 0.52 mmol) in dichloromethane (1 ml). The mixture was stirred at room temperature for 24 hours, then the solvent was evaporated under reduced pressure. The residue was purified by flash column chromatography on silica gel, eluting with $CH_2Cl_2/CH_3OH/NH_3$; 95:5:0.5 and crystallized from EtOAc/hexane to give the piperazine as microcrystals (32 mg, 27%), mp 105°–108° C. $\delta_H(CDCl_3)$ 8.47(1H, br s), 7.73(1H, s), 7.38(1H, d J 8.4 Hz), 7.32–7.19(7H, m), 6.56(1H, br s), 3.7(4H, br s), 2.81(2H, m), 2.65(2H, m), and 2.6(4H, br s).

Elemental analysis for $C_{21}H_{23}N_3O \cdot 0.4H_2O$: Calculated: C, 74.05; H, 7.04; N, 12.34%. Found: C, 74.12; H, 6.78; N, 12.36%.

EXAMPLE 25

1-(Indole-5-carbonyl)-4-[2-(4-methanesulfonamidophenyl)ethyl]piperazine

In the manner described in Example 24, indole-5-carboxylic acid (100 mg, 0.62 mmol) and 1-[2-(4-methanesulfonamidophenyl)ethyl]piperazine (180 mg, 0.64 mmol) gave, after purification by flash column chromatography on silica gel, eluting with $CH_2Cl_2/MeOH/NH_3$; 95:5:0.5 and trituration with hexane/EtOAc, the piperazine (68 mg, 26%), mp 94°–97° C. Elemental analysis for $C_{22}H_{26}N_4O_3S \cdot 0.5H_2O$: Calculated: C, 60.66; H, 6.26; N, 12.86%. Found: C, 61.02; H, 6.19; N, 12.51%.

EXAMPLE 26

1-(Indole-5-carbonyl)-4-[2-(4-nitrophenyl)ethyl]piperazine

In the manner described in Example 24, indole-5-carboxylic acid (100 mg, 0.62 mmol) and 1-[2-(4-nitrophenyl)ethyl]piperazine (151 mg, 0.64 mmol) gave, after purification by flash column chromatography on silica gel, eluting with $CH_2Cl_2/MeOH/NH_3$; 95:5:0.5 and trituration with hexane/EtOAc, the piperazine (38 mg, 16%), mp 204°–206° C.

Elemental Analysis for $C_{21}H_{22}N_4O_3 \cdot 0.5H_2O$: Calculated: C, 65.09; H, 6.00; N, 14.46%. Found: C, 65.14; H, 5.77; N, 14.38%.

EXAMPLE 27

1-(5,6-Dihydro-4H-thieno[2,3-b]thiopyran-4-oxo-6-carbonyl)-4-(4-nitrophenethyl)piperazine A solution 5,6-Dihydro-4H-thieno[2,3-b]thiopyran-4-oxo-6-carboxylic acid (850 mg, 3.9 mmoles) in DMF (5 mL) was treated with solid carbonyldiimidazole (772 mg, 4.76 mmole) at room temperature. The reaction was stirred at room temperature until all of the solid dissolved and 4-nitrophenylethyl piperazine (1.05 g, 4.76 mmoles) was then added in one portion and the reaction stirred at room temperature overnight.

The reaction was poured into 100 mL $H_2O$ and extracted with ethyl acetate. The ethyl acetate solution was dried over $MgSO_4$, filtered and concentrated in vacuo. The residue was chromatographed on silica gel eluting with 10% MeOH/chloroform to give 750 mg product which solidified on standing. The product was recrystallized from $CH_2Cl_2$/ethanol to give 640 mg; mp 176° C.

Elemental analysis for $C_{20}H_{20}N_3O_4S_2$. Calculated: C, 55.79; H, 4.68; N, 9.76. Found: C, 55.76; H, 5.03; N, 9.76.

The compounds of the following Examples 28 and 29 were prepared in a manner analogous to that described in Example 27.

EXAMPLE 28

1-(5,6-Dihydro-4H-thieno[2,3-b]thiopyran-4-oxo-6-carbonyl)-4-(2-(2-pyridinyl)ethyl)piperazine dihydrochloride Elemental analysis for $C_{19}H_{20}N_3O_2S_2 \cdot 2HCl \cdot \frac{1}{4}H_2O$: Calculated: C, 49.18; H, 4.88; N. 9.05. Found: C, 49.28; H, 5.02; N, 9.13; mp. 210° C.

EXAMPLE 29

1-(5,6-Dihydro-4H-thieno[2,3-b]thiopyran-4-oxo-6-carbonyl)-4-(4-nitrobenzyl)piperazine Elemental analysis for $C_{19}H_{18}N_3O_4S_2 \cdot \frac{1}{4}H_2O$: Calculated: C, 54.20; H, 4.42; N, 9.98. Found: C, 54.40; H, 4.49; N, 10.02. mp 182° C.

EXAMPLE 30

5-Methanesulfonamido-3-(1-[2-pyridylethyl]-4-piperidinyl-carbonyl)benzothiophene hydrogen oxalate A solution of 5.00 g (0.028 mol) of 5-nitrobenzothiophene (Bordwell, J. Am. Chem. Soc., 77, 5939 (1955)) in 175 mL of ethanol was hydrogenated at 50 psi over 0.5 g of 10% Pd/c for 1.5 hours. The catalyst was removed by filtration, and the solvent was removed under reduced pressure. The residue, 4.39 g, was dissolved in a mixture of 8.4 g of pyridine and 50 mL of methylene chloride. The solution, treated with 3.45 g (0.03 mol) of methanesulfonyl chloride, was stirred overnight at room temperature. The solution was washed with water, dried over $MgSO_4$, filtered, and the solvent removed under reduced pressure to give 1.74 g of crystalline 5-methanesulfonamidobenzothiophene.

To a suspension of 3.86 g (0.029 mol) of anhydrous aluminum chloride in 7 mL of methylene chloride was added 1.74 g (0.0078 mol) of 5-methanesulfonamidobenzothiophene followed by the careful addition of a solution of the acid chloride of 1-benzoyl-isonipecotic acid. (The latter solution was prepared by stirring 1.81 g of 1-benzoylisonipecotic acid with 3 mL of thionyl chloride and 3 drops of DMF for 18 hours, evaporating the solvents, and dissolving the residue in 10 mL of $CH_2Cl_2$.) The aluminum chloride reaction mixture was stirred vigorously at reflux for 2 hours, cooled, and poured onto 25 g of ice. The oil that precipitated was extracted into ethyl acetate. Evaporation of the ethyl acetate afforded 2.34 g of yellow foam. This material was stirred and refluxed with 30 mL of methanol and 45 mL 6N hydrochloric acid for 8 hours. Evaporation of the solvents and trituration of the residue with hot absolute ethanol gave 0.80 g of 5-methanesulfonamido-3-([4-piperidinyl]-carbonyl)benzothiophene hydrochloride; mp 259°-261° C.

A mixture of 0.80 g (0.00213 mole) of the piperidine derivative, 0.45 g (0.00427 mol) of 2-vinylpyridine, 0.435 g (0.0032 mol) of sodium acetate trihydrate, 2 mL of water and 2 mL of methanol was stirred and refluxed for 15 hours. The solution was evaporated to dryness and the residue was purified by flash chromatography on silica gel using 5% $CH_3OH$ in chloroform saturated with ammonia as an eluant. The chromatographically homogeneous fractions were combined. An oxalate salt, prepared in isopropyl alcohol-ethanol, was recrystallized from water to five the title compound, mp. 206°-208° C. Anal. Calc'd. for $C_{22}H_{25}N_3O_3S_2 \cdot 2C_2H_2O_4$: C, 50.07; H, 4.69; N, 6.74. Found: C, 50.05; H, 4.61; N, 6.76.

EXAMPLE 31

6-Methanesulfonamido-2-(1-[4-methanesulfonamidophenoxy ethyl]-4-piperidyl)indan-1-one oxalate hydrate Employing the procedures substantially as described in Example 23, Step C but employing the appropriate starting materials, the title compound was obtained.

Elemental analysis for $C_{24}H_{31}N_3O_6S_2 \cdot (COOH)_2 \cdot H_2O$ Calculated: C, 49.59; H, 5.60; N, 6.67. Found: C, 49.61; H, 5.27; N, 6.56. mp. 130°-135° C.

EXAMPLE 32

In Vitro Test for Class III Antiarrhythmic Activity

Purpose

This in vitro assay is designed to assess possible potassium channel blocking activity of a compound based on its ability to prolong effective refractory period (ERP) in isolated papillary muscle.

Tissue Preparation

Ferrets (700 to 1200 grams) are anesthetized with 0.7 ml of a mixture of xylazine and ketamine HCL in 1:7 ratio. Papillary muscles from the right ventricle are quickly excised from the isolated heart and mounted in 50 ml organ baths containing Krebs-Henseleit solution (pH=7.2-7.4) at 37° C. The composition of the solution in millimoles per liter are as follows: NaCl, 118; KCl, 4.7; $NaHCO_3$, 23; $CaCl_2 \cdot 2H_2O$ 2.0; $MgSO_4 \cdot 7H_2O$, 1.2; $KH_2PO_4$, 1.2; Dextrose, 11.1. Timolol ($10^{-7}$M) is added to the solution to block the effects of catecholamines released during stimulation of the muscles. This solution is aerated with 95% $O_2$ and 5% $CO_2$. The tissue is stimulated at 1 Hz at one msec pulse duration by a square wave stimulator at a voltage 30% above threshold through platinum electrodes that touch the tissue just above the bottom attachment point. The tendenous end of the tissue is connected by thread to an isometric force transducer leading to a polygraph.

Effective Refractory Period (ERP) Measurement

The ERP is determined by a standard 2 pulse protocol. Both pulses are stimulated at 1.3× voltage threshold. While pacing the tissue at a basal frequency of 1 Hz, a single extrastimulus is delivered after a variable time delay. The shortest delay resulting in a propagated response is defined as the ERP.

Protocol

1. Tissues are mounted with a resting tension of 0.5 gms, stimulated at 1 Hz, and allowed to equilibrate for 2 hours with washings at 15-20 minute intervals.
2. Voltage is adjusted to 30% above threshold and resting tension is adjusted for maximum developed tension, and the tissue is allowed 5 min. reequilibration time.
3. Effective refractory period is measured at 1 Hz. Changes in resting tension and developed force are noted.
4. After equilibration, ERP's and developed force are measured at 30 minutes following the addition of increasing cumulative concentrations for test agent to the organ bath. Four to five concentrations of test agents were used to generate a concentration-response curve.
5. Four tissues per compound are tested.

Results

Employing the above protocol it has been found that the effective concentration of most of the compounds of this invention required to increase the refractory period by an increment of 25% above base-line is less than or equal to 10 micromolar, i.e. $EC_{25} \leq 10$ μM, whereas sotalol in the same protocol has an $EC_{25} \sim 20$ μM.

What is claimed is:

1. A compound of structural formula:

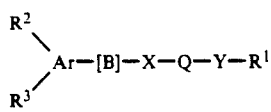

or a pharmaceutically acceptable salt thereof, wherein:
Ar is an aromatic ring selected from;
  (1) benzo,
  (2) thieno,
  (3) furo, and
  (4) pyrrolo;
B is benzo or other carbocyclic or heterocyclic moiety of 5-7 members fused to the aromatic ring, Ar, with up to 3 variable members independently selected from:
  (1) S—(O)$_p$, wherein p is 0, 1 or 2,
  (2) C(R)$_2$ wherein the R groups are the same or different and represent hydrogen or C$_{1-5}$ alkyl,
  (3) C=O,
  (4) CHOR,
  (5) —O—, and
  (6) NR;
Q is piperidine;
X is —CO—, —CO—NR—(CR$_2$)$_m$—, —SO$_2$— or —(CR$_2$)$_m$—, wherein m is 0, 1, 2 or 3;
Y is —(CR$_2$)$_n$—, wherein n is 0, 1, 2 or 3;
R$^1$ is pyridyl, benzimidazolyl, pyrimidinyl, phenyl, naphthyl, thienyl, thiazolyl, pyrazinyl, quinolinyl, quinoxalinyl, indolyl, or benzofuranyl, either unsubstituted or substituted with one or more of R$^2$, R$^3$ or R$^5$, wherein:
R$^5$ is
  (1) —N(R)SO$_2$C$_{1-6}$alkyl;
  (2) —N(R)SO$_2$(CH$_2$)$_m$CO$_2$C$_{1-6}$alkyl;
  (3) —NO$_2$;
  (4) —N(R)COC$_{1-6}$alkyl;
  (5) —N(R)SO$_2$—C$_6$H$_4$—R;
  (6) —N(R)COC$_6$H$_4$R;
  (7) —C$_{2-6}$alkanoyl;
  (8) CON(R)$_2$;
  (9) —CN;
  (10) —CO$_2$C$_{1-6}$alkyl;
  (11) benzoyl, either unsubstituted or substituted with C$_{1-6}$alkyl, C$_{1-6}$alkoxy, halo, or hydroxy;
  (12) —NRCOO(C$_{1-6}$alkyl);
  (13) —NRCOOphenyl either unsubstituted or substituted with C$_{1-6}$alkyl, C$_{1-6}$alkoxy, hydroxy or halo;
  (14) —NRCON(R)$_2$;
  (15) —S(O)$_p$C$_{1-6}$alkyl, wherein p is 0, 1 or 2;
  (16) —S(O)$_p$phenyl, either unsubstituted or substituted with C$_{1-6}$alkyl, C$_{1-6}$alkoxy, hydroxy, or halo;
  (17) phenyl, either unsubstituted or substituted with C$_{1-6}$alkyl, C$_{1-6}$alkoxy, halo, or hydroxy;
  (18) imidazolyl; or
  (19) —SO$_2$N(R)$_2$;
R$^2$ and R$^3$ are independently selected from:
  (1) hydrogen;
  (2) C$_{1-3}$alkyl either unsubstituted or substituted with
    (a)—N(R)$_2$
    (b)—CON(R)$_2$
    (c)—CO(C$_{1-6}$alkyl),
    (d)—O(C$_{1-6}$alkyl),
    (e)—OH, or
    (f)—S(O)$_p$(C$_{1-6}$alkyl);
  (3) C$_{1-3}$ alkoxy;
  (4) —N(R)$_2$;
  (5) halo; or
  (6) CF$_3$;
with the proviso that if R$^1$ is phenyl, with other than an R$^5$ substitutent, then one of R$^2$ or R$^3$ in the

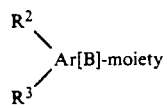

is R$^5$.

2. The compound of claim 1 wherein B has the structure;

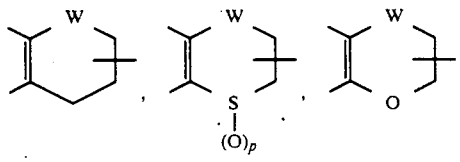

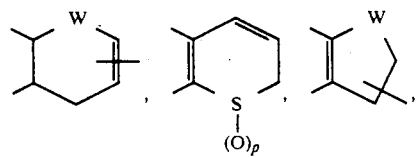

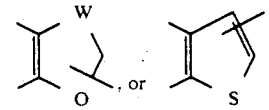

wherein W is >C=O, >CH$_2$ or >CHOH.

3. The compound of claim 2 wherein B has the structure:

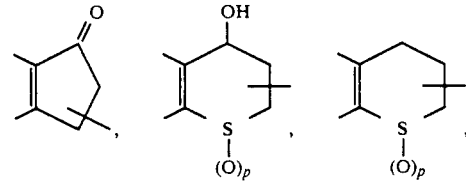

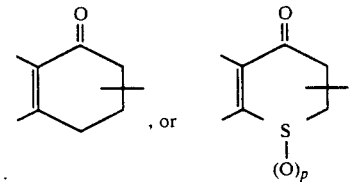

4. The compound of claim 3 wherein R$^1$ is pyridyl, benzimidazolyl, pyrimidinyl or phenyl, either unsubstituted or substituted with up to three substituents selected from R$^2$, R$^3$ and R$^5$.

5. The compound of claim 4 wherein R$^1$ is 2-pyridyl, 6-methyl-2-pyridyl or sunfonamidophenyl.

6. A pharmaceutical formulation comprising a carrier and an effective antiarrhythmic amount of a compound of claim 1.

7. The formulation of claim 6 comprising, in addition, an effective amount of a Class I, II or IV antiarrhythmia agent.

8. A method of treating arrhythmia and atrial and ventricular fibrillation in a patient with myocardial infarction, thereby preventing sudden death which comprises administering to such patient an antiarrythmic amount of a compound of claim 1.

9. A compound selected from:
2-[1-(2-pyridylethyl)-4-piperidyl]-1-indanone;
2-[1-(4-nitrophenethyl)-4-piperidyl]-1-indanone;
2-[1-(4-methanesulfonamidophenethyl)-4-piperidyl]-1-indanone;
6-methanesulfonamido-2-(1-[2-pyridylethyl]-4-piperidyl)indan-1-one;
6-methanesulfonamido-2-(1-[4-methanesulfonamidophenylethyl]-4-piperidyl)indan-1-one;
5-methanesulfonamido-3-(1-[2-pyridylethyl]-4-piperidinyl-carbonyl)benzothiophene; and
6-methanesulfonamido-2-(1-[4-methanesulfonamidophenoxyethyl]-4-piperidyl)indan-1-one;
or a pharmaceutically acceptable salt thereof.

* * * * *